(12) United States Patent
Elghazzawi

(10) Patent No.: US 11,528,771 B2
(45) Date of Patent: Dec. 13, 2022

(54) RESPONSE SYSTEM WITH EMERGENCY RESPONSE EQUIPMENT LOCATOR

(71) Applicant: ZOLL Medical Corporation, Chelmsford, MA (US)

(72) Inventor: Ziad F Elghazzawi, Newton, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 260 days.

(21) Appl. No.: 15/450,194

(22) Filed: Mar. 6, 2017

(65) Prior Publication Data
US 2017/0273116 A1 Sep. 21, 2017

Related U.S. Application Data

(63) Continuation of application No. 13/538,511, filed on Jun. 29, 2012, now abandoned.

(51) Int. Cl.
| | | |
|---|---|---|
| *H04W 76/50* | (2018.01) | |
| *H04W 4/02* | (2018.01) | |
| *G06Q 10/06* | (2012.01) | |
| *G06Q 10/08* | (2012.01) | |
| *G06Q 50/22* | (2018.01) | |
| *H04W 4/90* | (2018.01) | |
| *G16H 40/20* | (2018.01) | |

(52) U.S. Cl.
CPC ............ *H04W 76/50* (2018.02); *G06Q 10/06* (2013.01); *G06Q 10/08* (2013.01); *G16H 40/20* (2018.01); *H04W 4/023* (2013.01); *H04W 4/90* (2018.02)

(58) Field of Classification Search
CPC ............ G07C 9/00111; G08B 3/1083; H04W 76/007; H04W 4/22
USPC .......................................... 340/8.1
See application file for complete search history.

(56) References Cited

U.S. PATENT DOCUMENTS

| | | | |
|---|---|---|---|
| 5,348,008 | A | 9/1994 | Bornn et al. |
| 5,564,429 | A | 10/1996 | Bornn et al. |
| 5,593,426 | A | 1/1997 | Morgan et al. |
| 5,593,427 | A | 1/1997 | Gliner et al. |
| 5,607,454 | A | 3/1997 | Cameron et al. |
| 5,685,786 | A | 11/1997 | Dudley |
| 5,735,879 | A | 4/1998 | Gliner et al. |
| 5,752,976 | A | 5/1998 | Duffin et al. |
| 5,767,788 | A | 6/1998 | Ness |
| 5,836,993 | A | 11/1998 | Cole |

(Continued)

FOREIGN PATENT DOCUMENTS

| | | |
|---|---|---|
| WO | WO 2003/103765 | 12/2003 |
| WO | 2005/060301 | 6/2005 |

(Continued)

OTHER PUBLICATIONS

Extended European Search Report, European Patent Application No. 13809822.3, dated Jan. 12, 2016, 4 pages.

(Continued)

*Primary Examiner* — Yong Hang Jiang

(74) *Attorney, Agent, or Firm* — Zoll Medical Corporation

(57) ABSTRACT

This document relates to systems and techniques for providing response to emergency situations, such as traffic accidents, cardiac arrest, or other medical emergencies. The systems and techniques include systems and techniques for identifying and accessing emergency response equipment during a medical emergency.

28 Claims, 8 Drawing Sheets

(56) References Cited

U.S. PATENT DOCUMENTS

| | | |
|---|---|---|
| 5,879,374 A | 3/1999 | Powers et al. |
| 6,141,584 A | 10/2000 | Rockwell et al. |
| 6,208,897 B1 | 3/2001 | Jorgenson et al. |
| 6,292,687 B1 | 9/2001 | Lowell et al. |
| 6,292,698 B1 | 9/2001 | Duffin et al. |
| 6,312,378 B1 | 11/2001 | Bardy |
| 6,321,113 B1 | 11/2001 | Parker et al. |
| 6,328,699 B1 | 12/2001 | Eigler et al. |
| 6,334,070 B1 | 12/2001 | Nova et al. |
| 6,356,785 B1 | 3/2002 | Snyder et al. |
| 6,397,104 B1 | 5/2002 | Miller et al. |
| 6,459,371 B1 | 10/2002 | Pike |
| 6,492,581 B1 | 12/2002 | Bradbury |
| 6,493,581 B2 | 12/2002 | Russell |
| 6,597,948 B1 | 7/2003 | Rockwell et al. |
| 6,774,838 B2 | 8/2004 | Sun |
| 6,882,307 B1* | 4/2005 | Gifford ............... G06Q 10/087 |
| | | 701/469 |
| 6,937,150 B2 | 8/2005 | Medema et al. |
| 6,942,625 B1 | 9/2005 | Bryant |
| 7,048,185 B2* | 5/2006 | Hart .................. G06Q 10/06 |
| | | 235/384 |
| 7,120,488 B2 | 10/2006 | Nova et al. |
| 7,231,258 B2 | 6/2007 | Moore et al. |
| 7,245,964 B2 | 7/2007 | Moore et al. |
| 7,277,752 B2 | 10/2007 | Matos |
| 7,289,029 B2 | 10/2007 | Medema et al. |
| 7,672,720 B2 | 3/2010 | Heath |
| 7,769,465 B2 | 8/2010 | Matos |
| 7,894,843 B2 | 2/2011 | Smart et al. |
| 8,423,128 B2 | 4/2013 | Goto |
| 8,532,764 B2 | 9/2013 | Duke |
| 8,548,584 B2 | 10/2013 | Jorgenson |
| 8,559,913 B2 | 10/2013 | Thijs et al. |
| 8,666,488 B2 | 3/2014 | Duke |
| 8,682,284 B2 | 3/2014 | Brackett et al. |
| 2003/0233129 A1 | 12/2003 | Matos |
| 2004/0124979 A1* | 7/2004 | Medema ............... A61N 1/3904 |
| | | 340/539.18 |
| 2004/0128065 A1 | 7/2004 | Taylor et al. |
| 2004/0266390 A1 | 12/2004 | Faucher et al. |
| 2005/0102005 A1* | 5/2005 | Krig .................... A61N 1/3708 |
| | | 607/29 |
| 2005/0143776 A1 | 6/2005 | Brown |
| 2006/0026170 A1* | 2/2006 | Kreitler ............... G06F 16/904 |
| 2006/0084043 A1 | 4/2006 | Weaver et al. |
| 2007/0108274 A1 | 5/2007 | Boardman et al. |
| 2007/0218869 A1 | 9/2007 | Thijs et al. |
| 2008/0138778 A1 | 6/2008 | Eggert et al. |
| 2009/0051502 A1* | 2/2009 | Craik ................... G06Q 10/06 |
| | | 340/10.51 |
| 2009/0063234 A1 | 3/2009 | Refsland et al. |
| 2009/0222539 A1 | 9/2009 | Lewis et al. |
| 2009/0284348 A1* | 11/2009 | Pfeffer ................ G08B 25/006 |
| | | 340/7.3 |
| 2010/0190468 A1* | 7/2010 | Scott .................... H04M 1/2745 |
| | | 455/404.2 |
| 2010/0250643 A1 | 9/2010 | Savage et al. |
| 2011/0071880 A1 | 3/2011 | Spector |
| 2011/0117878 A1* | 5/2011 | Barash ............... G08B 21/0211 |
| | | 455/404.2 |
| 2012/0242483 A1 | 9/2012 | Kuo et al. |
| 2013/0053063 A1* | 2/2013 | McSheffrey ............ G01S 1/02 |
| | | 455/456.1 |
| 2013/0076508 A1 | 3/2013 | Goto |
| 2014/0002241 A1* | 1/2014 | Elghazzawi ........... H04W 4/90 |
| | | 340/8.1 |
| 2019/0108317 A1* | 4/2019 | Nedic ................... G16H 40/20 |

FOREIGN PATENT DOCUMENTS

| | | |
|---|---|---|
| WO | WO 2009/136259 | 11/2009 |
| WO | WO2009/136259 | 11/2009 |
| WO | 2011/100454 | 8/2011 |

OTHER PUBLICATIONS

International Search Report and Written Opinion, PCT/US13/43060, dated Sep. 10, 2013, 10 pages.

* cited by examiner

RESPONSE SYSTEM WITH EMERGENCY RESPONSE EQUIPMENT LOCATOR

CROSS-REFERENCE TO RELATED APPLICATIONS

This application is a continuation under 35 U.S.C. §120 of U.S. patent application Ser. No. 13/538,511 filed Jun. 29, 2012. All subject matter set forth in the above referenced application is hereby incorporated by reference in its entirety into the present application as if fully set forth herein.

TECHNICAL FIELD

This document relates to computer-based systems and techniques for providing response to emergency situations, such as traffic accidents, cardiac arrest, or other medical emergencies.

BACKGROUND

Sudden health problems such as sudden cardiac arrest and injuries caused by accidents kill thousands of people and cause permanent injury every year. Fast and competent care can be essential to positive outcomes in such situations. For example, it is said that the chance of surviving a sudden cardiac arrest falls by ten percent for every minute in delaying effective treatment.

Emergency events like sudden cardiac arrests and accidents are generally responded to by organized emergency response units, such as ambulance or fire crews, and by laypeople who are immediately around the events so that they personally witness or offer assistance for the events.

SUMMARY

This document describes systems and techniques that may be used to alert responders about an emergency situation and assist the responders in obtaining emergency response equipment such as AEDs. In the systems and techniques described here, an emergency call may come into a dispatch service and the dispatch service (e.g., through an employed human dispatcher) mayenter the address for the call and may have a map of the area around the call brought up on a video monitor. The map may be populated with icons that represent the locations of registered responders (including lay responders) in the geographic area around the call. The dispatcher may then choose to notify one or more of the responders. Upon receiving a notification, each candidate lay responder may reply with an indication of whether they are willing and able to help with the call. If they indicate that they are willing to help, the system may automatically send to their mobile computing device a map that shows their current location, the location for the call (where the call is near the victim's location), a highlighted navigation route between their location and the location of the call, and possibly icons that indicate the locations of publicly-accessible emergency response equipment (first aid kits and automatic external defibrillators (AEDs)) that might be helpful in responding to the call. The information about the publicly-accessible emergency response equipment can include an indication of the status of the equipment. By including the status of the emergency response equipment, the rescuer will not waste time locating and accessing equipment that is not fully functional (e.g., equipment with a low battery).

In one or more of the systems and techniques described here, emergency response equipment (e.g., publicly-accessible equipment or non-publicly-accessible equipment) may be provided to the scene of an emergency by someone associated with the equipment (e.g., an owner or administrator). For example, upon receiving an emergency call, the dispatcher can enter the address for the call and may have a map of the area around the call brought up on a video monitor. The map may be populated with icons that represent the locations of registered emergency response equipment (e.g., registered AEDs), whose locations have been previously stored in a database. The database also includes information (e.g., contact information) with associated owners or administrators for the equipment. The owner or administrator is any person associated with the equipment that has agreed to be notified of an emergency in the area and potentially provide the emergency response equipment to the scene of the emergency upon request. The owner or administrator is not required to be trained in providing emergency medical assistance, but rather has agreed simply to bring the emergency response equipment to the scene of the emergency. Thus, no special training is needed for the owner or administrator of the equipment. Based on equipment in the vicinity of the emergency, the dispatcher may then choose to notify one or more of the owners or administrators associated with a particular one or with particular ones of the pieces of registered emergency response equipment and request that the owner or administrator bring the equipment to the scene of the emergency. Upon receiving a notification, each owners or administrators may reply with an indication of whether they are willing and able to provide the medical equipment. If they indicate that they are willing to help, the system may automatically send to their mobile computing device, a map that shows the location of the emergency.

Such systems and techniques can, in certain implementations, provide one or more advantages. For example, by identifying equipment owners or administrators in addition to responders in the vicinity of a victim or victims, the systems and techniques can reduce response time for an emergency, which can be critically important for cardiac arrest victims. For example, the equipment owners or administrators can provide necessary emergency response equipment (such as a defibrillator) while the responders can provide initial treatment to the victim, for example by administering CPR. In some examples, the responder can initiate treatment to the victim sooner because they do not need to spend time locating and obtaining the medical equipment. In some additional examples, responders may be shown the location of known publicly-accessible equipment and status of such equipment, so that they can determine which equipment is fully functional and get it on the way to tending to the victim. This can reduce the time required to obtain functional emergency response equipment.

In some aspects, a method includes receiving a request for emergency services and receiving information that identifies a location associated with the request, identifying, from among a plurality of individuals registered as potential responders, one or more registered individuals who are currently nearest to the identified location, identifying one or more pieces of emergency response equipment nearest to the identified location, identifying registered individuals associated with the identified emergency response equipment, and transmitting, to the one or more individuals registered as potential responders and to the registered individuals associated with the emergency response equipment, information that identifies the location.

Embodiments can include one or more of the following.

The method can also include transmitting to the one or more individuals registered as potential responders an invitation to respond to the request for emergency services, determining whether a first of the one or more individuals registered as potential responders has responded affirmatively to the invitation, and transmitting information that identifies the location to the first registered individual.

The method can also include transmitting to the one or more registered individuals associated with the identified emergency response equipment an invitation to respond to the request for emergency services by providing the emergency response equipment, determining whether a first of the one or more individuals associated with the identified emergency response equipment has responded affirmatively to the invitation, and transmitting information that identifies the location to the first individual associated with the identified emergency response equipment.

The method can also include registering a plurality of individuals as potential responders and registering a plurality of individuals associated with emergency response equipment.

The method can also include registering the plurality of potential responders and the plurality of individuals associated with emergency response equipment comprises posting a sign-up software application that is internet accessible, and registering volunteers from the public, for example, using the sign-up application.

In some additional aspects, a method for communicating information to medical responders can include receiving a request for emergency services and receiving information that identifies a location associated with the request, identifying, from among a plurality of individuals registered as potential responders, one or more registered individuals who are nearest to the identified location, and identifying one or more pieces of registered emergency response equipment nearest to the identified location, accessing status information associated with the emergency response equipment nearest to the identified location, filtering, based at least in part on the status information, the identified registered emergency response equipment to determine a subset of functional emergency response equipment; and transmitting, to the one or more registered individuals, information that identifies the location and identifies locations for the determined subset of functional emergency response equipment.

Embodiments can include one or more of the following.

The method can also include transmitting to the one or more individuals registered as potential responders an invitation to respond to the request for emergency services, determining whether a first of the one or more individuals registered as potential responders has responded affirmatively to the invitation, and transmitting information that identifies the location associated with the request to the first registered individual.

The method can also include registering a plurality of individuals as potential responders by posting a sign-up software application that is internet accessible, and registering volunteers from the public using the sign-up application.

The information that identifies locations for the determined subset of functional emergency response equipment can include a map having icons identifying the emergency response equipment.

The icons can be configured to provide status information for the emergency response equipment nearest to the location associated with the request for emergency services.

The icons can be color-coded to provide status information.

In some aspects, a method can include receiving a request for emergency services and receiving information that identifies a location associated with the request, identifying, from among a plurality of individuals registered as potential responders, one or more registered individuals who are currently nearest to the identified location, identifying one or more pieces of registered emergency response equipment nearest to the identified location, accessing status information associated with the identified one or more pieces of emergency response equipment, and transmitting, to the one or more registered individuals, information that identifies the location and identifies locations and status information for the identified one or more pieces of emergency response equipment.

Embodiments can include one or more of the following.

The method can include transmitting to the one or more individuals registered as potential responders an invitation to respond to the request, determining whether a first of the one or more individuals registered as potential responders has responded affirmatively to the invitation, and transmitting information that identifies the location to the first registered individual.

The method can also include registering a plurality of individuals as potential responders by posting a sign-up software application that is internet accessible, and registering volunteers, from the public, for example using the sign-up application.

The information that identifies locations for the determined subset of functional emergency response equipment can include a map having icons identifying the emergency response equipment, the icons being configured to provide the status information for the emergency response equipment.

Transmitting the information that identifies locations and status information for the emergency response equipment can include transmitting information to provide color-coded icons with the color of each icon being based on the status of the associated emergency response equipment.

In some aspects a computer program product includes instructions to cause a processor to receive a request for emergency services and receive information that identifies a location associated with the request, identify, from among a plurality of individuals registered as potential responders, one or more registered individuals who are currently nearest to the identified location, identify one or more pieces of emergency response equipment nearest to the identified location, identify registered individuals associated with the identified emergency response equipment, and transmit, to the one or more individuals registered as potential responders and to the registered individuals associated with the emergency response equipment, information that identifies the location.

Embodiments can include one or more of the following.

The computer program product can include instructions to cause the processor to transmit to the one or more individuals registered as potential responders an invitation to respond to the request for emergency services, determine whether a first of the one or more individuals registered as potential responders has responded affirmatively to the invitation, and transmit information that identifies the location to the first registered individual.

The computer program product can include instructions to cause the processor to transmit to the one or more registered individuals associated with the identified emergency response equipment an invitation to respond to the request for emergency services by providing the emergency response equipment, determine whether a first of the one or more individuals associated with the identified emergency response equipment has responded affirmatively to the invitation, and transmit information that identifies the location to the first individual associated with the identified emergency response equipment.

The computer program product can include instructions to cause the processor to register a plurality of individuals as potential responders and register a plurality of individuals associated with emergency response equipment.

The computer program product can include instructions to cause the processor to access status information associated with the identified one or more pieces of emergency response equipment; and transmit, to the one or more registered individuals, information that identifies the location associated with the request for emergency services and identifies locations and status information for the identified one or more pieces of emergency response equipment.

In some aspects, a system can include an equipment database that includes location information for emergency response equipment; a responder database that includes information about a plurality of individuals registered as potential responders; and a computer. The computer can be configured to receive a request for emergency services and receive information that identifies a location associated with the request, access the database that includes information about a plurality of individuals registered as potential responders to identify, from among the plurality of individuals registered as potential responders, one or more registered individuals who are currently nearest to the identified location, access the equipment database to identify one or more pieces of emergency response equipment nearest to the identified location and identify registered individuals associated with the identified emergency response equipment, and transmit, to the one or more individuals registered as potential responders and to the registered individuals associated with the emergency response equipment, information that identifies the location.

Embodiments can include one or more of the following.

The computer can be further configured to transmit to the one or more individuals registered as potential responders an invitation to respond to the request for emergency services, determine whether a first of the one or more individuals registered as potential responders has responded affirmatively to the invitation, and transmit information that identifies the location to the first registered individual.

The computer can be further configured to transmit to the one or more registered individuals associated with the identified emergency response equipment an invitation to respond to the request for emergency services by providing the emergency response equipment, determine whether a first of the one or more individuals associated with the identified emergency response equipment has responded affirmatively to the invitation, and transmit information that identifies the location to the first individual associated with the identified emergency response equipment.

The computer can be further configured to access status information associated with the identified one or more pieces of emergency response equipment; and transmit, to the one or more registered individuals, information that identifies the location associated with the request for emergency services and identifies locations and status information for the identified one or more pieces of emergency response equipment.

The details of one or more embodiments are set forth in the accompanying drawings and the description below. Other features and advantages will be apparent from the description and drawings, and from the claims.

DESCRIPTION OF DRAWINGS

Like reference symbols in the various drawings indicate like elements.

DETAILED DESCRIPTION

Figure 1A:
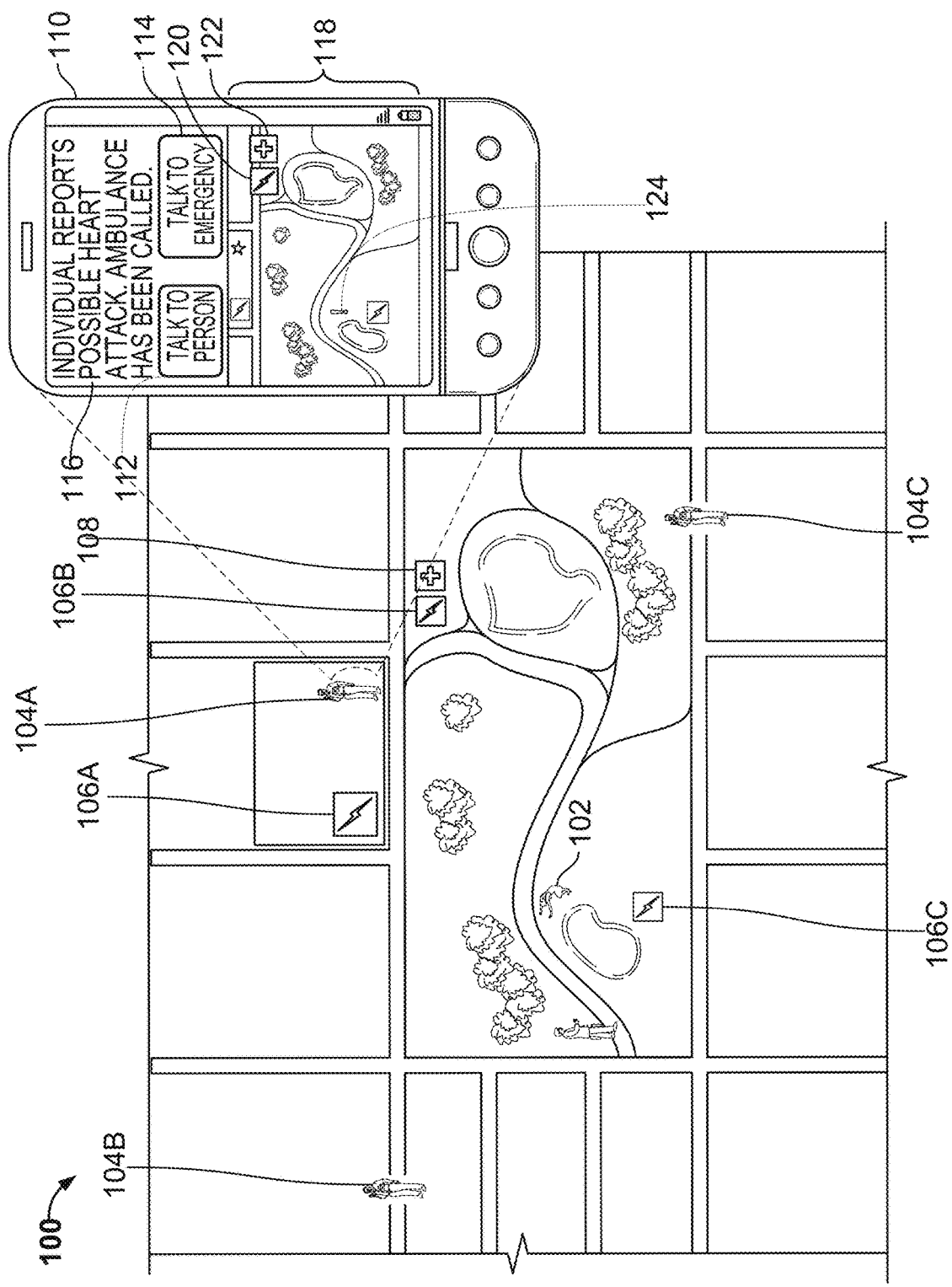
FIG. 1A is a conceptual diagram showing computer-guided emergency response by responders according to an example embodiment of the invention.

FIG. 1 is a conceptual diagram showing computer-guided emergency response by responders according to an example embodiment of the invention. In general, the figure shows a conceptualized version of a map for an area around a park in a metropolitan geographic area. An emergency event has recently occurred in the park, and various responders in the area of the event are shown converging on the location of the event. The map is overlaid with icons that represent various objects in the area, including a victim 102, various responder's 104A-C, and pieces of emergency response equipment 106A-C and 108. The figure also shows a representation of a screen for a smart phone 110 to indicate an example graphical user interface (GUI) that may be shown to a lay responder 104A who has chosen to volunteer to respond to a call in the area. The discussion with respect to this figure is intended to indicate in general ways how responders may be organized and notified, and how they may communicate with each other, in order to improve response to an emergency condition, such as a call about a person suffering from sudden cardiac arrest, or a mass emergency having multiple victims for which responder coordination is important. Examples of coordinating responders are described, for example, in U.S. patent application Ser. No. 12/946,803, filed on Nov. 15, 2010 and entitled "Community-Based Response System", the contents of which are hereby incorporated by reference in its entirety. While FIG. 1 illustrates the use of a smart phone 110 for communicating with responders, other mobile communication or computing devices could be used such as a laptop, phone, tablet, etc.

In the figure, the victim 102, has suffered a sudden cardiac arrest while running on a trail near a pond in the park. Upon feeling chest pains, the victim 102 may have called 911 in order to report an emergency, or may have activated an application installed on his or her smart phone, where the application is programmed to initiate a call to emergency services and to provide data that indicates the victim's 102 geographic location (e.g., as determined by the smartphone GPS or by using cell tower triangulation or similar services). Alternatively, the call to the central service may be made by telephone, either by the victim 102, or by a citizen who has come upon the victim 102 and has recognized that the victim 102 is in trouble. The dispatcher may then choose, at the dispatcher's discretion, to alert professional responders and registered responders who are registered with the system and who may be in the area around the park. As discussed in more detail below, the dispatcher, upon pulling up the map around the area of the victim 102, may choose to see an overlay, or layer, on the map of all possible registered responders in the area. From such an interface, the dispatcher can press on icons that represent certain potential responders to choose them as candidate responders, and may then make other selections to have notifications sent to each of those candidate responders regarding the emergency. A notification can then be sent to the candidate responders. For example, a message may be sent to each smart phone of the candidate responders.

Additionally, as discussed in more detail below, the dispatcher, upon pulling up the map around the victim 102 may choose to overlay or layer on the map all available emergency response equipment such as automatic external defibrillation devices (AEDs) in the area. The information about the available emergency response equipment can include the status of the emergency response equipment. For example, the map can be overlaid with color-coded icons associated with each piece of medical equipment where the color coding is indicative of the status. From such an interface, the dispatcher can press on the icons that represent certain potential emergency response equipment and then make a selection to have notifications sent to owners or administrators of the emergency response equipment to bring the emergency response equipment to the scene of the emergency and/or to provide information about the location and accessibility of the emergency response equipment to the responders responding to the emergency (e.g., by including the information in the notification sent to the responders).

In more particularly, the map in FIG. 1 shows iconic representation of equipment that is in the geographic area of the victim 102, and that may be accessible to responders who agree to help with the emergency situation. For example, icons having thunderbolts on them represent AEDs that a responder may grab and take to the victim 102 when the victim has suffered a sudden cardiac arrest. Icons having a "+" on them may represent first aid kits that responders could use to bandage or otherwise treat victims of an accident. As described more fully below, the existence and locations of the various pieces of equipment may initially be enrolled by owners of the equipment who want to make it available in emergency situations, and registered volunteers may periodically survey various areas to locate the equipment and to verify that it is still there, is operational, and is publicly accessible. Also, the equipment may include wireless functionality by which it reports itself in to a network, such as via a 3G interface, WiFi interface, Whispernet®-type interface and the like. An owner of such a device may then "open" the device to inspection by a lifesaving system, which may then periodically seek and receive reports on the current status of the device. In certain instances, such a system (which could be operated by a non-profit organization) may trade free monitoring of device status in exchange for the device owner agreeing to open the device for public use when it is needed.

The equipment may also be associated with a schedule during which it is available, so that the system may filter the display of equipment, so as not to show equipment that is not currently available. As one example, a coffee shop near the park may keep an AED near its counter where it cannot be stolen, but may be willing, as a gesture of good will, to have responders run into the shop and borrow the AED if it is needed in the area. Such an AED may be shown to responders on their devices if an emergency arises during the shop's hours of operation, but not shown after hours.

Figure 1B:
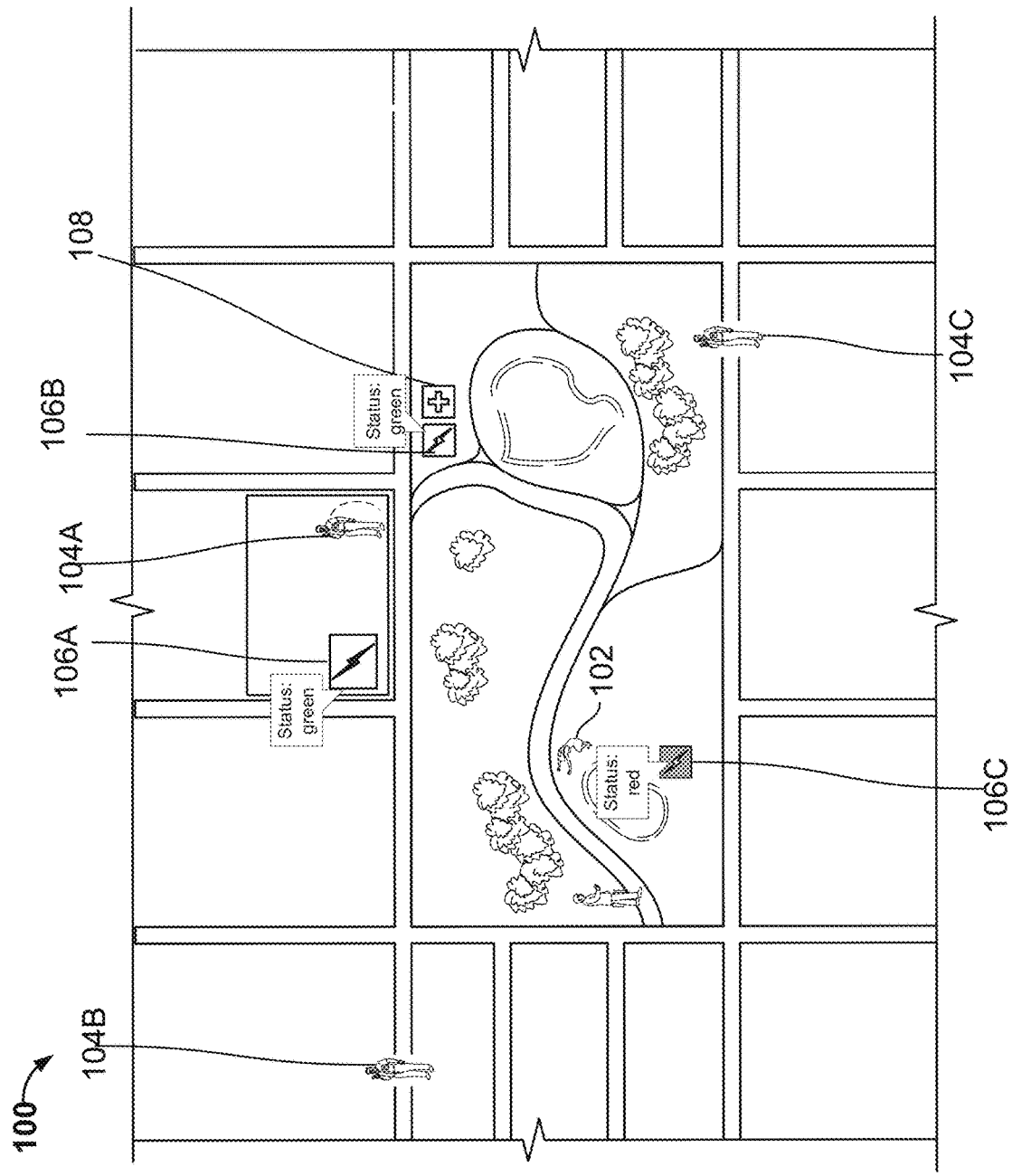
FIG. 1B is a conceptual diagram showing computer-guided emergency response by responders including status information emergency response equipment according to an example embodiment of the invention.

In some embodiments, for example as shown in FIG. 1B, the iconic representations of the equipment can include information about the status of the equipment. For example, the iconic representation can be color-coded to indicate whether the equipment is fully functional. In one particular example, a green color coding of the icon could be representative of equipment that has recently been tested and is fully functional, a red color coding can be representative of equipment that is not fully functional, and a yellow color coding could be representative of equipment that has not recently been tested but was previously functional at the time of the last test. In the particular example shown in FIG. 1B, AED 106C is color-coded to indicate that the AED is not functional. Thus, while AED 106C is the nearest AED to victim 102, upon seeing the status information a rescuer would know that this AED is not functional and locate the next nearest AED device (e.g., device 106B) rather than trying to use the nonfunctional AED 106C.

Referring now more specifically to the smart phone 110 of responder 104A, the screen of the smart phone 110 shows an example of what the responder 104A may see after she has been notified about the victim's 102 problem and has affirmatively responded that she would like to take part in the response thus converting herself from a candidate responder to a confirmed responder.

Upon the user 104A making such an indication, the dispatcher and/or a related automated system may download to the smart phone 110 information to allow the responder 104A to locate the victim 102, to show any relevant equipment in the area on the way to the victim 102, and to communicate to other responders who may be en route to helping the victim 102. Such information may be provided to the responder in a variety of manners, and in this example has been provided in the form of a webpage document that includes custom text about the victim 102, selectable controls by which the responder 104A may interoperate with the system, and a map with a navigational route to guide the responder 104A to the victim. The map includes information about emergency response equipment and the status of such equipment.

Referring now to the particular information displayed on the smart phone 110, and starting from the top of the display on the smart phone 110, there is shown a textual report 116 regarding the problem with the victim. Below the report 116, are two selectable controls 112 and 114. Selectable control 112, when selected by the responder 104A, will create a voice connection between the responder 104A and the victim 102. Selectable control 114, when selected, connects the responder 104A to whatever professional responders have been dispatched by the dispatch center and/or to the dispatcher. The bottom of the display for smart phone 110 is taken up by a map 118 which may be generated from a combination of data sources using known techniques such as those for creating mash-ups with Google Maps®. For example, the dispatch center may provide a latitude and longitude for responder 104A and a latitude and longitude for victim 102, to a navigation system that is publicly available (via a published application programming interface (API)), and a navigation system may respond by providing data for drawing the map overlaid with a thick navigation route line for an optimal path between the two points for the responder 104A. In addition, actual icons 120 and 122 are superimposed on the map to show the responder 104A where relevant equipment is located near their route between their current location and the victim 102. These icons can include visual indicia, such as color coding, to indicate the status of the medical equipment.

In some examples, the icons can include a selectable control that when selected connects the responder to an individual (e.g., a device owner or administrator) associated with the medical equipment. By connecting the responder with the individual associated with the medical equipment, the responder may be able to more quickly locate the equipment. For example, if an AED device is located behind the counter of a coffee shop, the icon on the responder's map may point to the responder to the coffee shop. However, without further information it may be difficult for the responder to locate the AED within the coffee shop. Thus, the voice communication can be beneficial in coordinating access to the emergency medical equipment.

Figure 5:
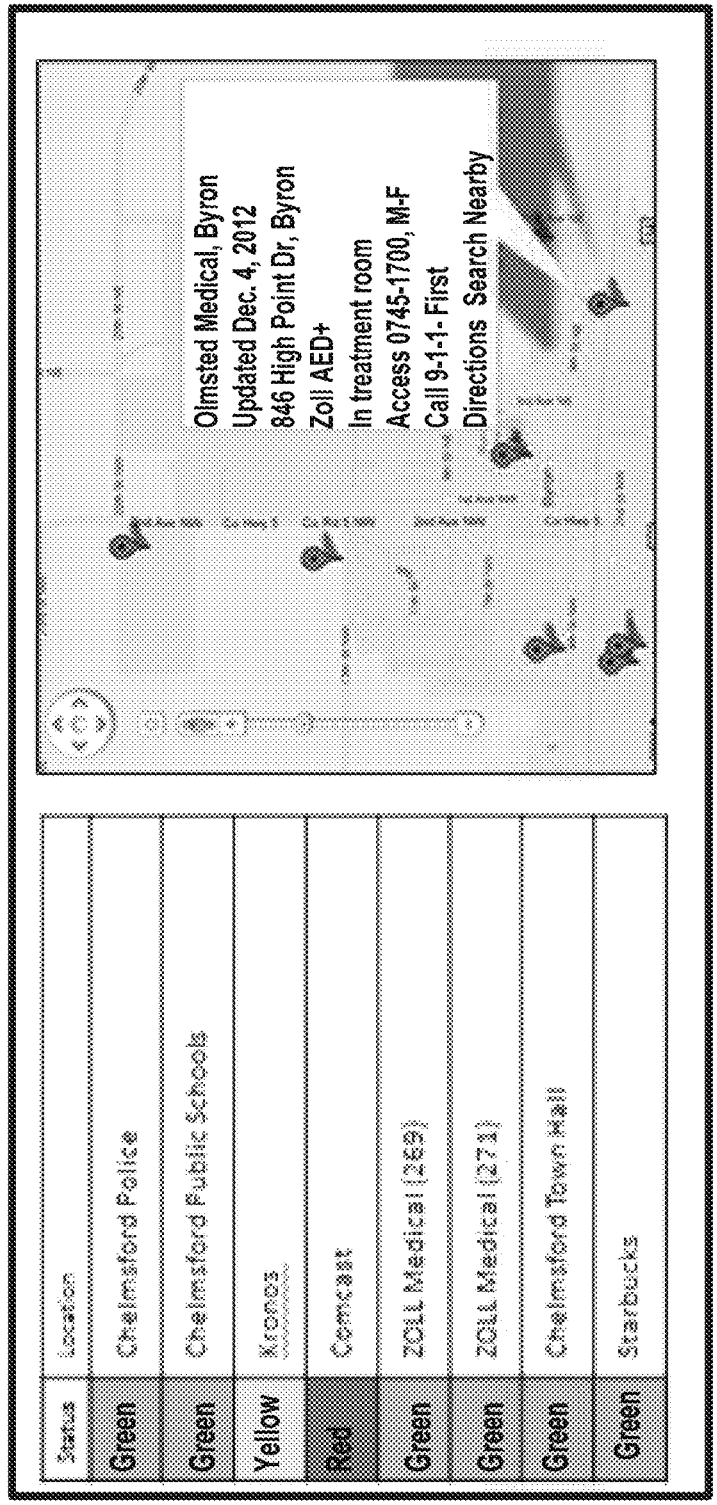

In some additional examples, the emergency response equipment icons can include selectable controls that, when selected, provide additional information about the medical equipment. For example, when the icon is selected additional information such as details about the location of the medical equipment, type and content of emergency response equipment available, and/or contact information for an individual associated with emergency response equipment can be displayed (e.g., as shown in FIG. 5).

The gathering of the information that is overlaid on the map may be by a server system before sending such information to the various client devices, or the server system may send information to the client devices, which may in turn automatically contact third-party mapping and navigation services (e.g., using their on-board applications and/or JavaScript provided to them by the server system) to generate the displays shown here.

In some examples, the potential responders may additionally include the owners or administrators of emergency response equipment such as AED units. In such examples, in addition to notifying responders, the operator also notifies the owners or administrators of the emergency response equipment. The owner or administrator can respond (e.g., in a manner similar to the responders) with whether he or she is available in willing to bring the emergency response equipment to the vicinity of the emergency. If so, information about the emergency, including a map to the location is sent to the owner or administrator.

Also, though the lay responder's device 110 is shown and described as a smart phone in this example, it may take a variety of other forms. For example, the device could be a cellular telephone having text messaging capabilities, so that the user can receive direction via text message. The device could also be a portable networked device that does not have direct telephony capabilities such as an iPod touch® media player or similar device. Other devices such as tablet PC's and other portable communication devices may also be used.

Figure 2:
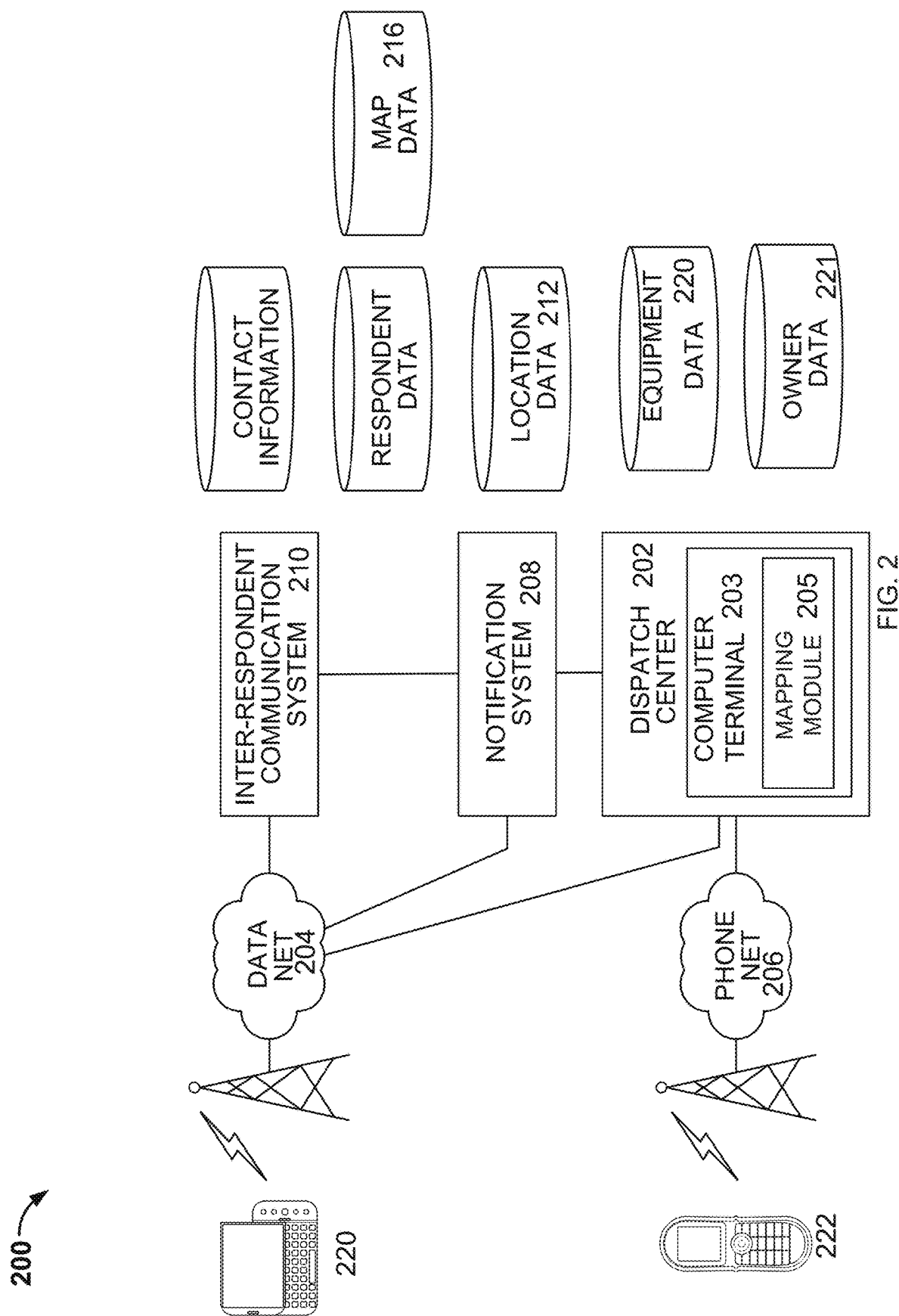
FIG. 2 is a block diagram of a system for coordinating lay response to emergency events according to an example embodiment of the invention.

FIG. 2 is a block diagram of a system 200 for coordinating responders to emergency events. In general, the system 200 shows various main sub-systems that can be used in an example to implement functionality like that described for FIG. 1 and below. The sub-systems are generally directed to receiving notification of an event that needs human responders, identifying responders in the area of the event, polling certain responders to see if they would like to be involved, and providing the responders who reply affirmatively with information to help them respond to the event. The sub-systems may also help coordinate the efforts of the responders or other individuals to coordinate the location and delivery of emergency response equipment such as AEDs to the scene of the emergency.

A central component of the system 200 is a dispatch center 202 such as a traditional emergency 911 dispatch center where operators (human or automated) receive calls about emergency events, take information on those calls, and notify appropriate professional responders so that they can respond to the calls. In this example, the dispatch center 202 is augmented with additional sub-systems to provide for greater functionality, including the dispatch of responders to emergency events and the coordination of delivery of emergency response equipment to the emergency event.

The dispatch center 202 can receive communications e.g., calls or data communications through telephone network 206 from basic telephones such as cellular telephone222 and/or through network 204 from mobile computing devices 220. Calls may also come into the dispatch center 202 via portable emergency response equipment worn by potential victims. The dispatch center 202 may also communicate with a notification system 208, which is designed to provide notifications to responders (lay responders and/or professional responders) about emergencies that may be occurring in their area and for which their intervention may be requested. The notification system 208, in performing these operations, may initially serve as an interface between a dispatcher at the dispatch center 202 and various candidate and confirmed responders who are using devices such as mobile computing device 220.

The notification system 208 may also manage an enrollment process by which responders register themselves with the system 208 and are managed by the system 208. The notification system 208, in performing its functions, may depend on and manage a number of sources of data. For example, location data 212 may be gathered from devices used by various responders who are enrolled with the system 208 to determine where the responders are located. Thus, for example, the notification system 208 may receive a query from the dispatch center 202 that identifies a location of an emergency and then use that location to identify enrolled responders who are currently in that same vicinity and whose devices are currently turned on and reporting their location. Such information may be made available voluntarily by the responders when they register with the system, so that they permit tracking of their current location for defined purposes and under defined conditions.

Map data 216 may also be stored by, or otherwise accessed by, notification system 208. The map data 216 may take the form of visual map tiles and data required to connect latitude/longitude coordinates or other such information to locations on the map. The map data 216 may also include data needed to generate navigational routes on maps, and also to convert English language (or other human language) addresses to more technical map identifiers such as latitude/longitude coordinates. While the map data 216 and other data are shown as being part of the notification system 208 in this example, they may also be accessed from other locations, such as from third-party services provided by companies like Google®, Yahoo!®, MapQuest®, and Microsoft® using API's that are public and generally familiar.

The notification system 208, in performing its functions, may additionally depend on emergency response equipment data to 220 and emergency response equipment owner data 221. The emergency response equipment data 220 can include information about the location of the emergency response equipment (e.g., the latitude and longitude, the physical location within a building, the common name of the building, the address of the location), availability of the emergency response equipment (e.g., if the equipment is only available during business hours or with other restrictions), type of equipment available (e.g., first aid supplies, portable defibrillators, or other medical instrumentation and supplies), and/or status information about the equipment. When a request for emergency services is received by the dispatch center, in addition to identifying available respondents, the dispatch center can additionally locate and identify emergency response equipment that may be useful for responding to the emergency. The location of the emergency response equipment can be overlaid on the map generated by the notification system 208.

The notification system 208 may additionally rely on emergency response equipment owner or administrator data 221. For example, similar to identifying respondents in the area, emergency response equipment owners or administrators can additionally be identified and contacted to provide emergency response equipment to the scene of the emergency. Such information may be made available voluntarily by the emergency response equipment owner or administrator when they register with the system, so that they permit such contact. Location of the equipment owners and administrators does not need to be tracked. Rather, such individuals can be people who are likely to be near the equipment. For example, if the equipment is located in an office building, the administrator or owner can be an employee having an office near the equipment. Thus, a particular piece of emergency response equipment can have multiple owners or administrators who are registered with the system as being likely to be near the equipment and willing to respond to an emergency.

An inter-responder communication system 210 may be provided as an adjunct to the notification system 208. The inter-responder communication system 210 may be provided to allow voice communications between responders and each other, between responders and a victim, and between other parties that may be involved in an emergency response operation such as the equipment owners and administrators.

As an example of the operation of system 200, a call may be initially received at the dispatch center 202 from telephone 222, such as through a 911 calling network. A dispatcher at the dispatch center 202 may speak to a caller on telephone 222 to find out that the caller is witnessing another person having a heart attack in the 600 block of Main Street. The dispatcher may begin to type information about the call into a computer terminal 203, including the text "600 block of Main Street", and such text entry may cause a map to be displayed on a computer display of the dispatcher, centered around the typed address.

The computer display may also show icons that represent all potential responders who are currently known to be in the area of the 600 block of Main Street (i.e., whose devices are on and reporting their locations) and to show all emergency response equipment known to be in the area. A mapping module (e.g., a mapping module in terminal 203) can obtain such information by accessing information from the notification system 208, and then plotting icons for potential responders and emergency response equipment on the dispatcher's computer monitor. Each of the icons for the potential responders may be supplemented with a small indicator that shows the type of responder that each person in the area is, such as a trained physician or a relatively inexperienced giver of CPR. Additionally, each of the icons for the emergency response equipment may be supplemented with an indicator of the equipment's current status and the type of equipment available.

The dispatcher may then select some of the identified responders in the area, such as by tapping their icons on a touchscreen computer interface, and may then select a control (e.g., click or tap an on-screen button) to have a notification generated for each of the selected responders, making them candidate responders. Similarly, the dispatcher may then select some of the identified emergency response equipment in the area, such as by tapping the icons for the emergency response equipment on a touch screen computer interface and may then select a control to have a notification generated to each of the owners or administrators of the medical equipment.

Figure 3A:
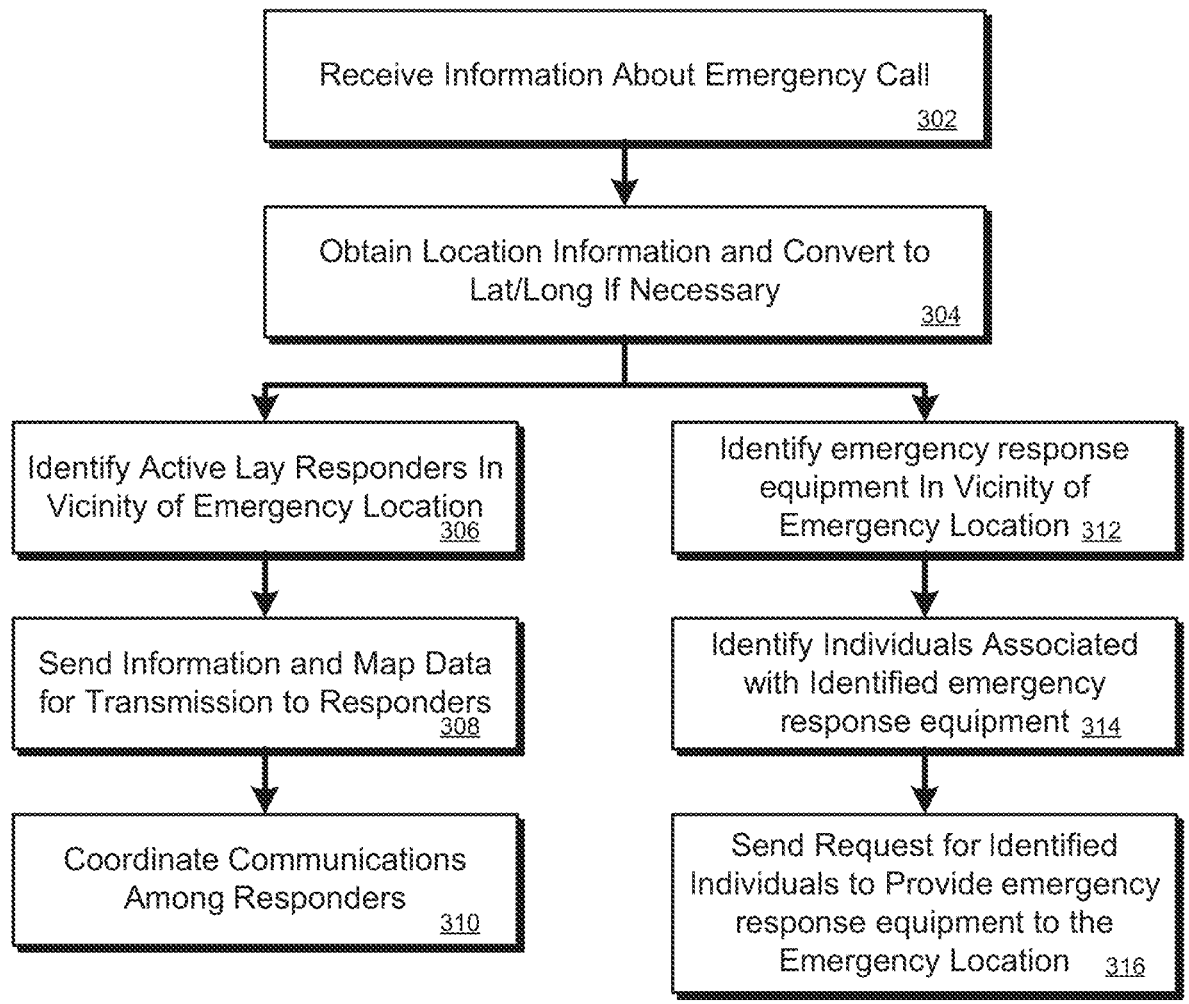
FIGS. 3A and 3B are flow charts of processes for organizing a response to an emergency call according to an example embodiment of the invention.

FIG. 3A is a flow chart of a process for organizing responders and individuals able to provide emergency response equipment such as AEDs to an emergency call according to an example embodiment of the invention. In general, the process involves identifying a number of lay respondents who have registered with a system and are in the vicinity of an incoming emergency event, identifying emergency response equipment in the vicinity of the incoming emergency event and identifying equipment owners or administrators associated with such equipment.

The process begins at box 302, where a system receives information about an emergency call. In one instance, the call may be a 911 call and the information may be entered into a computer terminal by an operator who answered the call. In other instances, the call may be a data transmission from a mobile computing device. In either situation, a location for an emergency event may be determined, such as by the operator typing in an address relayed by the caller, or by location information received with a data transmission (e.g., GPS data from a mobile computing device).

At box 304 a geographic determination component of a system (e.g., mapping module 205 in FIG. 2) obtains location information like that discussed above and converts it to a latitude/longitude coordinate or area. For example, a dispatcher's terminal may provide for parsing of text that the dispatcher types and any addresses that are identified in the text may be passed to a separate system that may turn the address into a latitude/longitude coordinate. In response, another system may be caused to transmit data to the dispatcher's terminal so that a map of the area around the event is displayed to the dispatcher.

At box 306, active responders in a vicinity of the emergency location are identified. For example, the same system that transmitted the map data to the dispatcher's terminal may also access a tracking sub-system that is aware of or can poll the locations of mobile computing devices for all people who are registered as potential responders with the process, who are in the vicinity of the emergency, and who have their devices turn on, reporting their current location. The possible responders may be determined using one or more of the methods described in U.S. patent application Ser. No. 12/946,803, filed on Nov. 15, 2010 and entitled "Community-Based Response System", the contents of which are hereby incorporated by reference in its entirety.

At box 308, the process sends information and map data for transmission to responders. In an embodiment, the process sends information and map data for transmission to other parties, for example, equipment owners or administrators associated with such equipment and/or caller. The information may include some basic information about the emergency and also information needed to generate an annotated map like that shown in FIGS. 1A and 1B. At box 310, the process coordinates communications among the responders.

At box 312, the process identifies emergency response equipment in the vicinity of the emergency location. For example, the same system that transmitted the map data to the dispatcher's terminal may also access stored information about emergency response equipment such as AEDs to determine which emergency response equipment is the vicinity of the emergency location. The operator can select one or more particular pieces of the emergency response equipment based on the type of emergency response equipment available, the distance from the emergency location, the type of emergency and/or the status of the medical equipment. Once the particular pieces of emergency response equipment have been identified, at box 314, the process identifies individuals associated with the identified medical equipment. For example, information about one or more individuals that are likely to be in the area of the emergency response equipment and have registered with the system as being willing to respond to an emergency event by providing the emergency response equipment to the scene of the emergency can be accessed. Once the relevant individuals have been identified, at box 316, the process sends a request to the identified individuals to provide the emergency response equipment to the emergency location. The information provided to the identified individuals may include some basic information about the emergency and also information needed to generate an annotated map like that shown in FIGS. 1A and 1B.

Figure 3B:
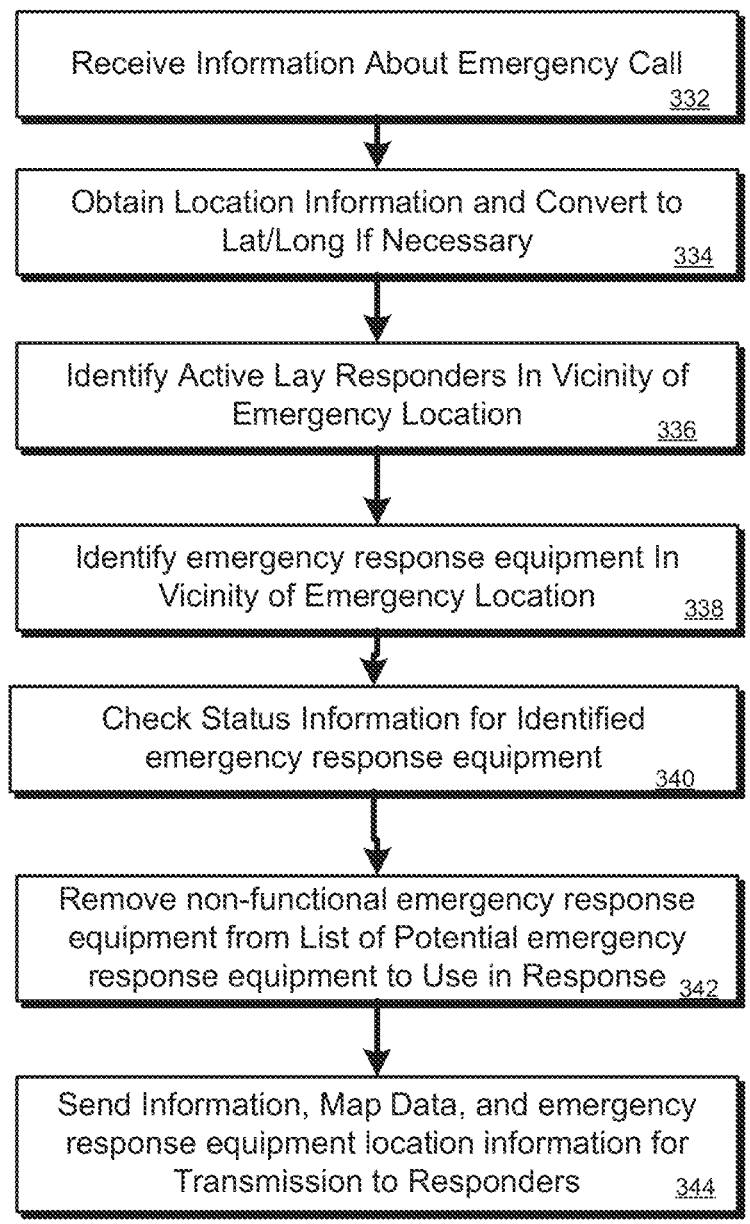

FIG. 3B is a flow chart of a process for organizing responders to an emergency call according to an example embodiment of the invention. In general, the process involves identifying a number of lay respondents who have registered with a system and are in the vicinity of an incoming emergency event and providing them with information about emergency medical equipment in the vicinity.

As described above in relation to FIG. 3A, system such as the dispatch center 202 in FIG. 2 receives information about an emergency call (box 332), obtains location information like that discussed and converts it to a latitude/longitude coordinate or area (box 334), and identifies active responders in the vicinity of the emergency location (box 336).

At box 338, the system identifies emergency response equipment in the vicinity of the emergency location. For example, the system that transmitted the map data to the dispatcher's terminal may also access stored information about emergency response equipment such as AEDs to determine which emergency response equipment is the vicinity of the emergency location. The operator can select one or more particular pieces of the emergency response equipment based on the type of emergency response equipment available, the distance from the emergency location, the type of emergency and/or the status of the medical equipment.

In some additional embodiments, the system can automatically select one or more pieces of emergency response equipment based on a distance from the vicinity of the emergency location.

In some additional examples, the system can automatically select a predetermined number of pieces of emergency response equipment based on the type of emergency to locate the nearest equipment to the emergency location regardless of the absolute distance. At box 340, the process checks status information for the identified medical equipment by accessing stored information about the equipment. This status information can include items such as the last date of servicing, the last known status of the equipment, the battery life of the equipment, and/or the like. At box 340, based on the status information for the medical equipment, the process removes nonfunctional emergency response equipment from the list of potential emergency response equipment for use in responding to the emergency. Only the functional emergency response equipment (e.g., based on the stored information) is identified as being available to responders. Thus, responders will not waste valuable time to obtain nonfunctional equipment. At box 344, the process sends information, map data and/or emergency response equipment location information for transmission to responders. In an embodiment, emergency response equipment location information is transmitted to a dispatch center such as dispatch center 202 of FIG. 2. The emergency response equipment location information may be present in a memory of the equipment, determined using GPS, or provided using another method known in the art. In an embodiment, the process sends information and map data for transmission to other parties, for example, equipment owners or administrators associated with such equipment and/or a caller. The information may include some basic information about the emergency and also information needed to generate an annotated map like that shown in FIGS. 1A and 1B including the identification of the locations for medical equipment.

Figure 4:
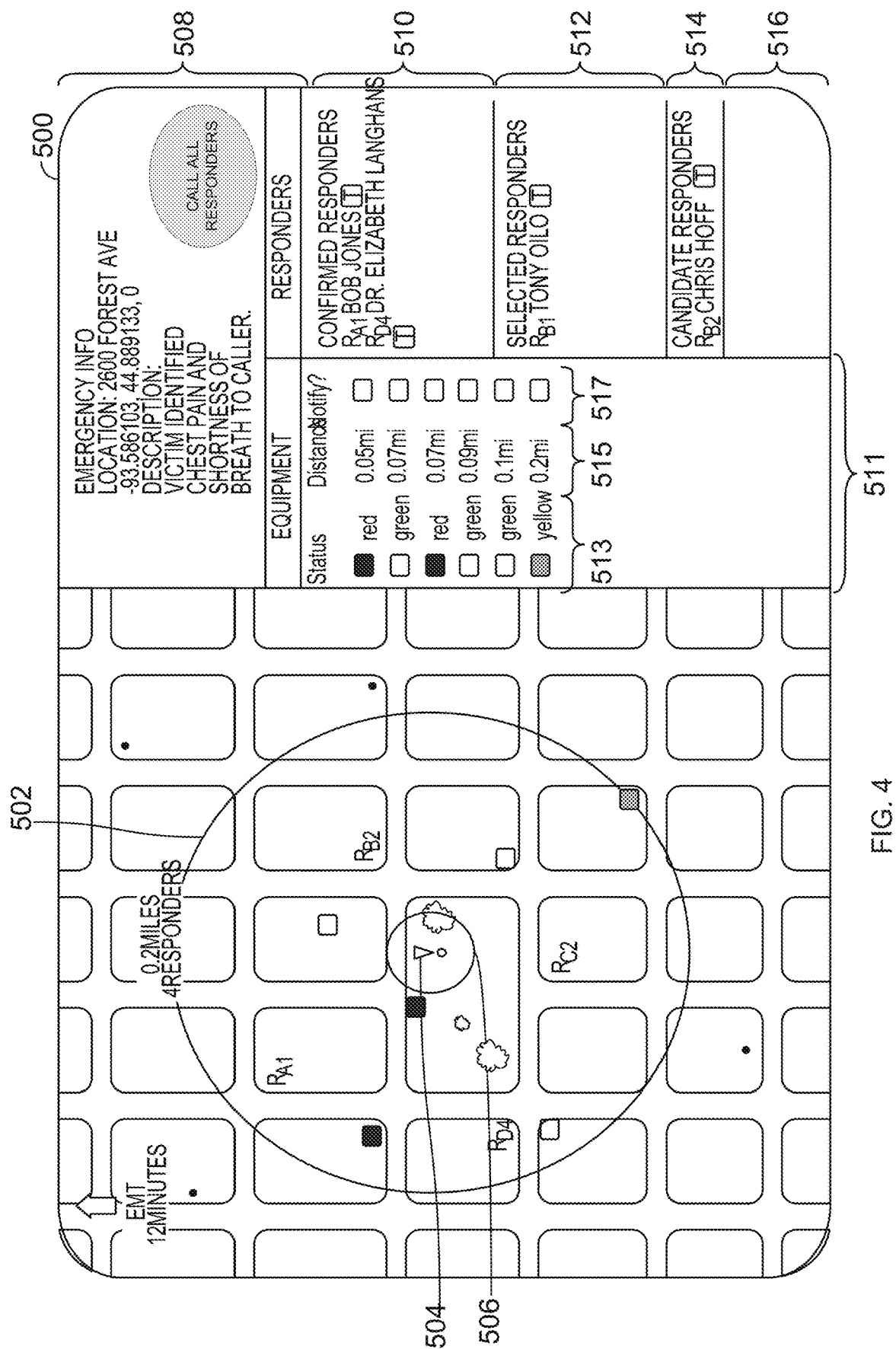
FIGS. 4 and 5 show exemplary screen shots for a dispatcher according to an example embodiment of the invention.

FIG. 4 shows an example screen shot for a dispatcher. In general, this screen shot provides an example of the type of data a dispatcher may see as the dispatcher selects responders and emergency medical equipment to respond to an emergency event that has been called in by telephone.

The screen in this example is split mainly into a map area and a data area. The map area is centered around a victim represented by icon 504, and may have been retrieved automatically when the dispatcher typed a location into their computer terminal. A circle 506 may be shown around the icon for the victim, showing a zone of uncertainty for the victim's location. A broader circle 502 indicates a candidate zone around the victim. This circle may circumscribe the area within which the system will look for potential responders and/or for emergency response equipment such as AEDs. The size of the initial circle may be selected automatically, such as to be a predetermined radius, or based on estimated time for responders to arrive at the victim. If the dispatcher does not see enough responders and/or emergency response equipment in the circle, the dispatcher may provide an input to change the size of the circle, such as by dragging the circle in or out on a touch screen display. In some examples, this size of the initial circle or the size of a revised circle can be different for the area used to identify responders as compared to the area used to locate emergency response equipment such as AEDs. For example, if the responders are tasked with bringing the emergency response equipment to the scene of the emergency, then the size of the area used to locate emergency response equipment may be smaller than the size of the area used to locate responders. In another example, if emergency response equipment owners or administrators are tasked with bringing the emergency response equipment the scene of the emergency, then the size of the area used to locate emergency response equipment may be larger than the size of the area used to locate responders because the responders can begin medical treatment such as CPR during the time used for the equipment owners or administrators to provide the medical equipment.

In the particular example, the initial circle can include an icon for responders and an icon for emergency medical equipment. An operator can click and drag the associated icon to revise the associated input area. For example, by clicking and dragging on an icon for responder, the operator can modify the area used to locate and identify responders, but will not modify the area used for locating emergency medical equipment.

In the data portion of the screen 500, and at the top, there is shown an emergency information area 508, where various data about an event may be displayed, such as the location of the victim (in plain English and lat/long), and a description of the event that the dispatcher may have entered upon receiving a call. Such a description may then be sent automatically to any responder that becomes confirmed in the system, or even to potential responders in an invitation. The area 508 also includes a selectable button that, when the dispatcher presses it and holds it down, causes the dispatchers speech to be broadcast to all responders (e.g., all confirmed lay responders and all professional responders), such as when the dispatcher wants to broadcast instructions to the team. Other similar controls may also be provided as needed.

A messages area 516 at the bottom of the data area provides a location in which a dispatcher can enter textual messages to be sent to the responders. Other data input and output may also be provided in one or more pop up boxes that may appear depending on the context of the system that the dispatcher is controlling.

The three remaining areas of the data area indicate the status of various responders in an area, coordinated with icons on the map area that show those responders. For example, in this display, candidate responder's area 514 shows responders in the relevant area who have not yet been acted on by the dispatcher. Here, there is one such responder named Chris Hoff, who is designated with a B2 subscript, indicating that he is the B responder on the map and he is a level 2 skill level, which may be a lay responder who is formally CPR certified. A "T" icon is shown next to his name, and the dispatcher may select that icon in order to talk by voice directly with him; the dispatcher could also push the icon and then type a message, and that message would be sent directly to Mr. Hoff.

The selected responder's area shows responders who have received an invitation to respond. A dispatcher may move someone from area 514 to area 512 by selecting their entry and then dragging it upward from one area to the next. Here, the dispatcher has selected a level 1 responder, which may be someone who has shown proficiency for CPR with a downloaded application but is not CPR certified. That user, Tony Oilo, has not yet responded. Although not shown, the entry could also be accompanied by a digital clock that shows the elapsed time since the responder has been invited so that, after a time, the dispatcher can cancel the invitation and invite a different candidate.

The confirmed responder's area 510 shows two responders who were invited and responded affirmatively, and thus are presumptively en route to the victim. These responders are again, a level 1 responder and a level 4 responder, who may be a general physician (where level 6 responders could be emergency room or critical care physicians). Dr. Langhans in this example is relatively close to the park where the victim is located, and thus may be expected to arrive there soon.

The emergency response equipment location section 511 includes information about the location, status, and availability of emergency response equipment such as AEDs in the vicinity of the emergency. The status information is shown in column 513, can be color-coded based on the status of the emergency response equipment as described herein. Other indicators such as textual indicators or symbolic indicators could be used to indicate the status of the emergency response equipment. As shown in column 515, the distance from the emergency location to the emergency response equipment can additionally be displayed. As shown in column 517, the user interface includes a selection mechanism that enables the operator to notify individuals associated with the emergency response equipment by selecting the notification button. For example, if the operator wanted to notify the owners of all emergency response equipment within one 10th of a mile from the emergency location, the operator could do so by clicking on the selectable input icons in column 517.

FIG. 5 shows an example screenshot for a dispatcher or responder. In general, this screenshot provides an example of the type of data a dispatcher or responder may see in relation to emergency medical equipment in the vicinity of an emergency. The information presented to the dispatcher or responder includes a map area that is centered around the victim and may have been automatically retrieved when the dispatcher typed a location into their computer terminal. Emergency response equipment in the vicinity of the emergency is identified by icons on the map. In addition to identifying the equipment locations, status information about the equipment is provided, for example, as shown in the color-coded status indicators on the left of the user interface. The status can additionally/alternatively be indicated with a textual indicator or symbolic indicator. In FIG. 5, both a color-coding and a textual indicator are shown. Additionally, when an individual selects a particular piece of medical equipment, additional information can be displayed to the user. For example, by clicking on one of the icons in the map, the user can view additional information such as more detailed location information, availability, and contact information.

Figure 6:
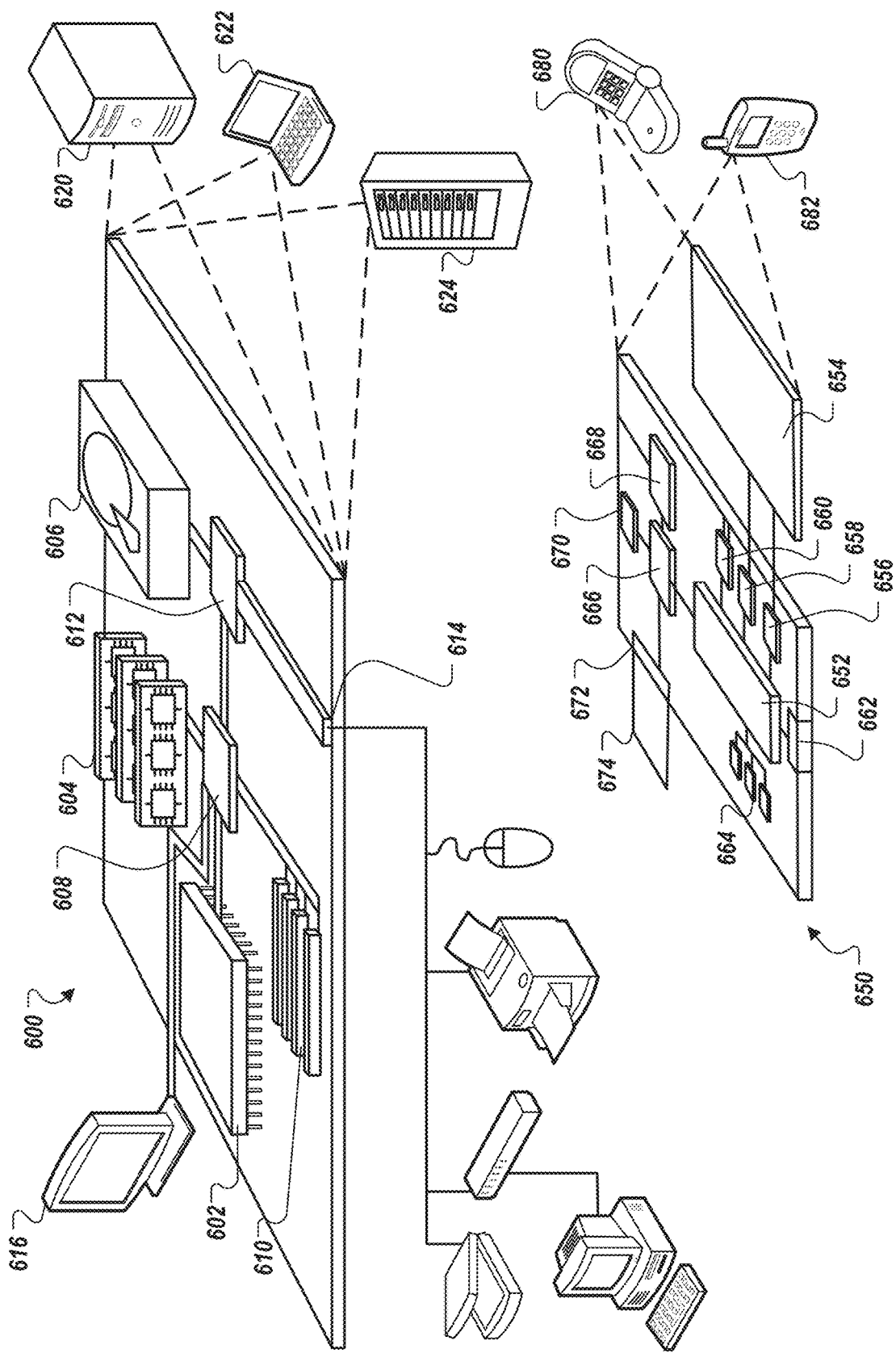
FIG. 6 shows an example of a generic computer device and a generic mobile computer device, which may be used with the techniques described herein.

FIG. 6 shows an example of a generic computer device 600 and a generic mobile computer device 650, which may be used with the techniques described here. Computing device 600 is intended to represent various forms of digital computers, such as laptops, desktops, workstations, personal digital assistants, servers, blade servers, mainframes, and other appropriate computers. Computing device 650 is intended to represent various forms of mobile devices, such as personal digital assistants, cellular telephones, smartphones, and other similar computing devices. The components shown here, their connections and relationships, and their functions, are meant to be exemplary only, and are not meant to limit implementations of the inventions described and/or claimed in this document.

Computing device 600 includes a processor 602, memory 604, a storage device 606, a high-speed interface 608 connecting to memory 604 and high-speed expansion ports 610, and a low speed interface 612 connecting to low speed bus 614 and storage device 606. Each of the components 602, 604, 606, 608, 610, and 612, are interconnected using various busses, and may be mounted on a common motherboard or in other manners as appropriate. The processor 602 can process instructions for execution within the computing device 600, including instructions stored in the memory 604 or on the storage device 606 to display graphical information for a GUI on an external input/output device, such as display 616 coupled to high speed interface 608. In other implementations, multiple processors and/or multiple buses may be used, as appropriate, along with multiple memories and types of memory. Also, multiple computing devices 600 may be connected, with each device providing portions of the necessary operations (e.g., as a server bank, a group of blade servers, or a multi-processor system).

The memory 604 stores information within the computing device 600. In one implementation, the memory 604 is a volatile memory unit or units. In another implementation, the memory 604 is a non-volatile memory unit or units. The memory 604 may also be another form of computer-readable medium, such as a magnetic or optical disk.

The storage device 606 is capable of providing mass storage for the computing device 600. In one implementation, the storage device 606 may be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product may also contain instructions that, when executed, perform one or more methods, such as those described above. The information carrier is a computer- or machine-readable medium, such as the memory 604, the storage device 606, memory on processor 602, or a propagated signal.

The high speed controller 608 manages bandwidth-intensive operations for the computing device 600, while the low speed controller 612 manages lower bandwidth-intensive operations. Such allocation of functions is exemplary only. In one implementation, the high-speed controller 608 is coupled to memory 604, display 616 (e.g., through a graphics processor or accelerator), and to high-speed expansion ports 610, which may accept various expansion cards (not shown). In the implementation, low-speed controller 612 is coupled to storage device 606 and low-speed expansion port 614. The low-speed expansion port, which may include various communication ports (e.g., USB, Bluetooth, Ethernet, wireless Ethernet) may be coupled to one or more input/output devices, such as a keyboard, a pointing device, a scanner, or a networking device such as a switch or router, e.g., through a network adapter.

The computing device 600 may be implemented in a number of different forms, as shown in the figure. For example, it may be implemented as a standard server 620, or multiple times in a group of such servers. It may also be implemented as part of a rack server system 624. In addition, it may be implemented in a personal computer such as a laptop computer 622. Alternatively, components from computing device 600 may be combined with other components in a mobile device (not shown), such as device 650. Each of such devices may contain one or more of computing device 600, 650, and an entire system may be made up of multiple computing devices 600, 650 communicating with each other.

Computing device 650 includes a processor 652, memory 664, and an input/output device such as a display 654, a communication interface 666, and a transceiver 668, among other components. The device 650 may also be provided with a storage device, such as a microdrive or other device, to provide additional storage. Each of the components 650, 652, 664, 654, 666, and 668, are interconnected using various buses, and several of the components may be mounted on a common motherboard or in other manners as appropriate.

The processor 652 can execute instructions within the computing device 650, including instructions stored in the memory 664. The processor may be implemented as a chipset of chips that include separate and multiple analog and digital processors. The processor may provide, for example, for coordination of the other components of the device 650, such as control of user interfaces, applications run by device 650, and wireless communication by device 650.

Processor 652 may communicate with a user through control interface 658 and display interface 656 coupled to a display 654. The display 654 may be, for example, a TFT LCD (Thin-Film-Transistor Liquid Crystal Display) or an OLED (Organic Light Emitting Diode) display, or other appropriate display technology. The display interface 656 may comprise appropriate circuitry for driving the display 654 to present graphical and other information to a user. The control interface 658 may receive commands from a user and convert them for submission to the processor 652. In addition, an external interface 662 may be provided in communication with processor 652, so as to enable near area communication of device 650 with other devices. External interface 662 may provide, for example, for wired communication in some implementations, or for wireless communication in other implementations, and multiple interfaces may also be used.

The memory 664 stores information within the computing device 650. The memory 664 can be implemented as one or more of a computer-readable medium or media, a volatile memory unit or units, or a non-volatile memory unit or units. Expansion memory 674 may also be provided and connected to device 650 through expansion interface 672, which may include, for example, a SIMM (Single In Line Memory Module) card interface. Such expansion memory 674 may provide extra storage space for device 650, or may also store applications or other information for device 650. Specifically, expansion memory 674 may include instructions to carry out or supplement the processes described above, and may include secure information also. Thus, for example, expansion memory 674 may be provided as a security module for device 650, and may be programmed with instructions that permit secure use of device 650. In addition, secure applications may be provided via the SIMM cards, along with additional information, such as placing identifying information on the SIMM card in a non-hackable manner.

The memory may include, for example, flash memory and/or NVRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 664, expansion memory 674, memory on processor 652, or a propagated signal that may be received, for example, over transceiver 668 or external interface 662.

Device 650 may communicate wirelessly through communication interface 666, which may include digital signal processing circuitry where necessary. Communication interface 666 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 668. In addition, short-range communication may occur, such as using a Bluetooth®, WiFi, or other such transceiver (not shown). In addition, GPS (Global Positioning System) receiver module 670 may provide additional navigation- and location-related wireless data to device 650, which may be used as appropriate by applications running on device 650.

Device 650 may also communicate audibly using audio codec 660, which may receive spoken information from a user and convert it to usable digital information. Audio codec 660 may likewise generate audible sound for a user, such as through a speaker, e.g., in a handset of device 650. Such sound may include sound from voice telephone calls, may include recorded sound (e.g., voice messages, music files, etc.) and may also include sound generated by applications operating on device 650.

The computing device 650 may be implemented in a number of different forms, as shown in the figure. For example, it may be implemented as a cellular telephone 680. It may also be implemented as part of a smartphone 682, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other.

A number of embodiments have been described. Nevertheless, it will be understood that various modifications may be made without departing from the spirit and scope of the invention. For example, much of this document has been described with respect to smartphones and similar client devices, but other forms of devices may be employed, including jackets for portable devices where the jackets have been provided with some or all of the functionality just described. In some examples, the dispatch center could be implemented on a mobile computer such as an iPhone®. In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other embodiments are within the scope of the following claims.

What is claimed is:

1. A medical equipment management system comprising:
   an equipment information database for emergency response equipment comprising first aid kits and defibrillators, the equipment information database comprising:
   status information in three categories,
   the status information comprising battery life information for the emergency response equipment comprising the first aid kits and the defibrillators, and
   the three categories comprising:
   (a) currently fully functional,
   (b) previously functional at a time of a last test, and
   (c) not fully functional, and
   location information for the emergency response equipment comprising the first aid kits and the defibrillators, the location information comprising one or more of: a physical location within a building, a name of the building, and global positioning system (GPS) information,
   contact information for an owner or administrator of the emergency response equipment; and
   a notification system communicatively coupled to the equipment information database and configured to communicatively couple to an emergency dispatch center and at least one mobile device associated with a responder, the notification system comprising processor executable instructions configured to cause one or more processors to:
   access the equipment information database,
   receive an emergency event location, for an emergency event, from the emergency dispatch center,
   receive a current location of the at least one mobile device associated with the responder,
   identify emergency response equipment in a vicinity of the emergency event,
   provide, to the emergency dispatch center, the location information for the emergency response equipment in the vicinity of the emergency event supplemented with the status information based on the three categories for the emergency response equipment in the vicinity of the emergency event, and provide a map at the at least one mobile device associated with the responder, the map comprising:
the emergency event location, and
responder-selectable visual location indicators at emergency response equipment locations on the map along a route between the current location of the responder and the emergency event location, and
in response to a selection of a particular responder-selectable visual location indicator, provide, at the at least one mobile device associated with the responder, the contact information for the emergency response equipment in the vicinity of the emergency event that corresponds to the particular responder-selectable visual location indicator selected from the map by the responder.

2. The system of claim 1 wherein the processor executable instructions are configured to cause the one or more processors to select a quantity of the emergency response equipment to identify as in the vicinity of the emergency event.

3. The system of claim 1 wherein the processor executable instructions are configured to cause the one or more processors to identify the emergency response equipment in the vicinity of the emergency event based on the emergency event location and the location information for the emergency response equipment.

4. The system of claim 3 wherein the processor executable instructions are configured to cause the one or more processors to identify the emergency response equipment in the vicinity of the emergency event based on a desired distance between the emergency event location and an emergency response equipment location as indicated by the location information for the emergency response equipment.

5. The system of claim 4 wherein the desired distance between the emergency event location and the emergency response equipment location is a predetermined distance.

6. The system of claim 4 wherein the desired distance between the emergency event location and the emergency response equipment location is a based on a travel time of the responder.

7. The system of claim 4 wherein the desired distance between the emergency event location and the emergency response equipment location is adjustable based on a quantity of defibrillators in an area with a radius corresponding to the desired distance.

8. The system of claim 1 wherein the equipment information database comprises availability information that includes times that the emergency response equipment is available for use.

9. The system of claim 8 wherein the processor executable instructions are configured to cause the one or more processors to provide the availability information to one or more of the emergency dispatch center and the at least one mobile device associated with the responder.

10. The system of claim 1 wherein the status information comprises one or more of a last date of testing and a last known test result.

11. The system of claim 1 wherein the processor executable instructions are configured to cause the one or more processors to monitor the status information.

12. The system of claim 1 wherein the map comprises navigation information.

13. The system of claim 1 wherein the location information includes mapping information comprising visual map tiles and data configured to connect latitude and longitude coordinates to locations on the visual map tiles.

14. The system of claim 1 wherein the processor executable instructions are configured to cause the one or more processors to receive medical information for a victim from the emergency dispatch center and to provide the medical information for the victim to the at least one mobile device associated with the responder.

15. The system of claim 1 wherein the processor executable instructions are configured to cause the one or more processors to access a responder tracking system, wherein the responder tracking system is configured to determine the current location of the at least one mobile device associated with the responder.

16. The system of claim 1 wherein the processor executable instructions are configured to cause the one or more processors to provide one or more of graphical and textual data to the at least one mobile device associated with the responder.

17. The system of claim 8 wherein the processor executable instructions are configured to cause the one or more processors to exclude unavailable emergency response equipment from the map based on the availability information.

18. The system of claim 3 wherein the processor executable instructions are configured to cause the one or more processors to identify the emergency response equipment in the vicinity of the emergency event based on the status information.

19. The system of claim 1 wherein the processor executable instructions are configured to cause the one or more processors to exclude non-functional emergency response equipment from the map based on the status information.

20. The system of claim 8, wherein the one or more processors are configured to provide the availability information at the at least one mobile device associated with the responder in response to the selection of the particular responder-selectable visual location indicator.

21. The system of claim 1, wherein the status information comprises first aid supply information for at least one first aid kit.

22. The system of claim 1, wherein the map includes an indicator of a type of emergency response equipment, the type comprising one or more of a first aid kit and a defibrillator.

23. The system of claim 1 wherein the responder-selectable visual location indicators are color-coded based on the three categories of the status information.

24. The system of claim 23, wherein the responder-selectable visual location indicators are green for the currently fully functional category and yellow for the previously functional at the time of the last test category.

25. The system of claim 1 wherein the location information for the emergency response equipment comprises a street address.

26. The system of claim 1 wherein the processor executable instructions are configured to cause the one or more processors to exclude unavailable emergency response equipment from the location information provided to the emergency dispatch center.

27. The system of claim 1 wherein the processor executable instructions are configured to cause the one or more processors to exclude non-functional emergency response equipment from the location information provided to the emergency dispatch center.

28. The system of claim 1 wherein the processor executable instructions are configured to cause the one or more processors to, in response to a selection of a particular responder-selectable visual location indicator, provide, at the at least one mobile device associated with the responder, one or more of location details and equipment type and content information for the emergency response equipment in the vicinity of the emergency event that corresponds to the particular responder-selectable visual location indicator selected from the map by the responder.

* * * * *